United States Patent [19]

Sadanandam et al.

[11] Patent Number: 6,130,352

[45] Date of Patent: *Oct. 10, 2000

[54] METHOD FOR PRODUCING (+) (2S,3S)-3-(2-AMINOPHENYLTHIO)-2-HYDROXY-3(4'-METHOXYPHENYL)-PROPIONIC ACID

[75] Inventors: Yennu Sangiah Sadanandam, Secunderabad; Meera Manjaya Shetty, Hyderabad; Imtiaz Ahm Ansari, Hyderabad; Jhillu Singh Yadav, Hyderabad; Alla Venkata Rama Rao, Hyderabad, all of India

[73] Assignee: Council of Scientific & Industrial Research, New Delhi, India

[ * ] Notice: This patent issued on a continued prosecution application filed under 37 CFR 1.53(d), and is subject to the twenty year patent term provisions of 35 U.S.C. 154(a)(2).

[21] Appl. No.: 08/826,004

[22] Filed: Mar. 27, 1997

Related U.S. Application Data

[63] Continuation of application No. 08/379,133, Jan. 27, 1995, abandoned.

[51] Int. Cl.[7] .......................... C07B 55/00; C07C 321/28
[52] U.S. Cl. ............................. 562/401; 562/431
[58] Field of Search ...................... 562/401, 431

[56] References Cited

U.S. PATENT DOCUMENTS

| | | | |
|---|---|---|---|
| 4,416,819 | 11/1983 | Nagao et al. | 260/293.3 B |
| 4,533,748 | 8/1985 | Manghisi et al. | 562/401 |
| 4,939,295 | 7/1990 | Merli et al. | 562/401 |
| 5,013,834 | 5/1991 | Piselli | 540/491 |
| 5,218,142 | 6/1993 | Godfrey, Jr. et al. | 562/506 |
| 5,302,741 | 4/1994 | Lidor et al. | 560/7 |

OTHER PUBLICATIONS

CA 106: 33134g (1986).
E.J.Corey and John Mann, A New Stereocontrolled Synthesis of Prostaglandins via Prostaglandin $A_2$, Journal of the American Chemical Society, Oct. 3, 1973, pp. 6832–6833.
Merck Research Laboratories, The Merck Index, 1996, p. 1031.

*Primary Examiner*—Shailendra Kumar
*Assistant Examiner*—Brian J. Davis
*Attorney, Agent, or Firm*—Volpe and Koenig, P.C.

[57] ABSTRACT

A process for the preparation of (+) (2S, 3S)-3-(2-aminophenylthio)-2-hydroxy-3-(4'-methoxyphenyl)-propionic acid which comprises treating the (±) compound of (2RS, 3RS) 3-(2-aminophenylthio)-2-hydroxy-3-(4'-methoxyphenyl)-propionic acid (formula (II)) with the (+) compound of the 2-methylbenzylamine (formula (III)) and an alkali in the presence of a polar solvent, the amount of the compound of the formula (III) and the alkali being in half equivalent amount of compound of the formula (II) employed, separating the precipitate (+) amine salt form of (2-aminophenylthio)-2-hydroxy-3-(4'-methoxyphenyl)-propionic acid from the 1(−) salt form remaining in solution, by known methods treating the (+) amine salt from with an organic solvent and then decomposing the (+) amine salt form to produce (+)(2s, 3s)-3-(2-aminophenylthio)-2-hydroxy-3-(4'-methoxyphenyl)-propionic acid.

16 Claims, 1 Drawing Sheet

(+)-(2S,3S)

FORMULA I (±)-(2RS,3RS)

FORMULA II

D(+)-α-Methylbenzylamine

FORMULA III

METHOD FOR PRODUCING (+) (2S,3S)-3-(2-AMINOPHENYLTHIO)-2-HYDROXY-3(4'-METHOXYPHENYL)-PROPIONIC ACID

This application is a continuation of application Ser. No. 08/379,133, filed Jan. 27, 1995 now abandoned.

This invention relates to an improved method for the preparation of (+) (2S,3S)-3-(2-aminophenylthio)-2-hydroxy-3-(4'-methoxyphenyl)-propionic acid. The (+)(2S,3S)-3-(2-aminophenylthio)-2-hydroxy-3-(4'-methoxyphenyl)propionic acid prepared by the process of the present invention is a key intermediate for the synthesis of diltiazem. The (+) (2S,3S)-3-(2-aminophenylthio)-2-hydroxy-3-(4'-methoxyphenyl)propionic acid prepared by the process of the invention is represented by the general formula (I) shown in the drawings accompanying this specification.

BACKGROUND OF THE INVENTION

The above compound of the formula (I) is an important key intermediate for the synthesis of a drug having potent calcium channel blocking activity and has been clinically used as an effective antianginal and antihypertensive agent whose generic name is Diltiazem (Merck Index, X Edition N, 3189, page 466). The compound of the formula (II) has two asymmetric carbon atoms, at the positions 2 and 3. Thus, it can have two types of stereoisomers, namely the threo and the erythro forms. The threo form has two optical isomers. Normally it is obtained as a racemic mixture, but by reacting with an optically active α-methylbenzylamine of the formula (III) in a solvent the two diastereomer salts can be optically resolved using their differences in a solubility. The compound of the formula (I) is currently prepared by the optical resolution of (2RS,3RS)(2-aminophenylthio)-2-hydroxy-3-(4'-methoxyphenyl)propionic acid of the formula (II) treating it with half equimolar amount of optically active (+)α-methylbenzylamine represented by the general formula (III) as resolving agent and alkali in the presence of a polar solvent as described in Example 1. The requisite (+)α-methylbenzylamine is commercially available.

Inone et al (Yakugaku Zasshi, 93, 279, 1973) reported by the optical resolution of (±) compound of the formula (II) using cinchonidine. The less soluble cinchonidine salt of the formula (II) however, was the unwanted (2R,3R)isomer and the desired (2S,3S)isomer was obtained from the mother liquor. This process has the drawback of the requirement of a large quantity of expensive cinchonidine.

The main object of the present invention is to provide an improved process for the optical resolution of (2RS,3RS)-3-(2-aminophenylthio)-2-hydroxy-3-(4'-methoxyphenyl)propionic acid which overcomes the drawbacks of the hitherto known process.

SUMMARY OF THE INVENTION

The object of the present invention is achieved by treatment of (±) compound of the formula (II) with half equimolar amount of (+) compound of the formula (III) and alkali in the presence of a polar solvent. The reaction readily caused precipitation of the (+)amine salt of the formula (I) and 1(−)salt remained in the solution. Similarly, when 1-form of amine of the formula (III) is used, the 1-form of the salt of the formula (I) separates out in the form of less soluble salt.

DETAILED DESCRIPTION OF THE INVENTION

Figure 1:
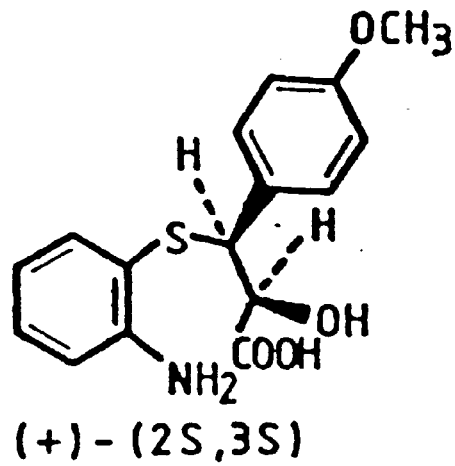
FIG. 1 is a symbolic representation of the (+) amine salt, referred to as Formula (I), produced in accordance with the process of the present invention.
Figure 2:
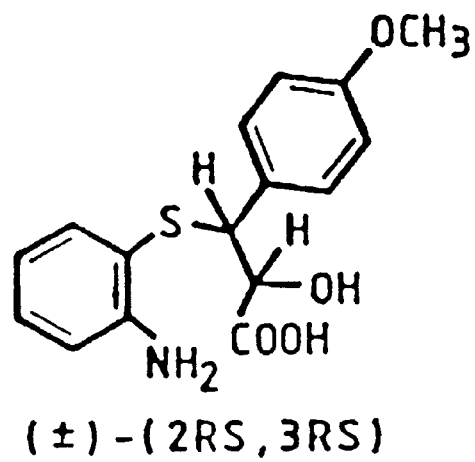
FIG. 2 is a symbolic representation, referred to as Formula (II), of the (±) compound from which the (+) salt of the Formula (I) is obtained using the method of the present invention.
Figure 3:
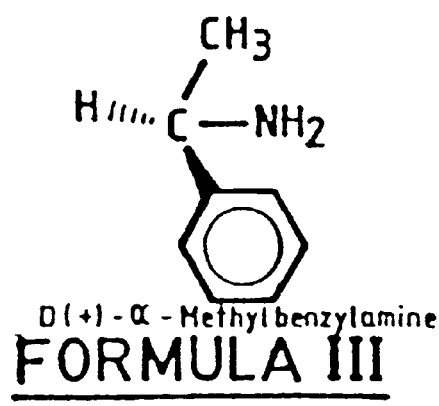
FIG. 3 is a symbolic representation of a compound, referred to as Formula (III), used in the process of the present invention.

The treatment of the (+)amine salt form of the formula (I) is treated with an organic solvent to give the optically pure (+)salt of (2S,3S) of the formula (I). The yield was found to be in 82% yield. The optical purity of the diastereomeric salt is usually higher than 95%. If the optical purity needs to be further improved, this can be done easily by recrystallization, for recrystallization, solvents such as water, hydrophilic organic solvents like methanol, ethanol, acetone mixtures of water may be used. The (+)amine salt of the formula (I) is decomposed by known methods.

Accordingly, the present invention provides an improved process for the preparation of (+)(2S,3S)-3-(2-aminophenylthio)-2-hydroxy-3-(4'-methoxyphenyl) proponic acid of the formula (I) shown in the drawing accompanying this specification which comprises treating (±)compound of the formula (II) with (+)compound of the formula (III) and an alkali in the presence of a polar solvent, the amount of the compound of the formula (III) and the alkali being in half equivalent amount of the compound of the formula (II) employed, separating the precipitate of the (+)amine salt form of the formula (I), from the 1(−)salt remaining in the solution, by known methods, treating the (+)amine salt form of the formula (I) with an organic solvent and thereafter decomposing the (+)amine salt form of the formula (I) to produce the (+)(2S,3S)-3-(2-aminophenylthio)-2-hydroxy-3-(4'-methoxyphenyl) propionic acid of the formula (I).

The alkali used may be selected from KOH, NaOH, LiOH and $NH_4OH$, though KOH is the preferred one.

The polar solvent used in the above reaction may be selected from water, hydrophilic organic solvents like methanol, ethanol, acetone, mixture of water and hydrophobic organic solvents like benzene, ethylacetate etc. However, the use of water is most advantageous from the view point of economy. The organic solvent used for the treatment of (+)amine salt form of the formula (I) may be selected from benzene, toluene and the like. The large differences in solubility of the two diastereomers, the small solubility of the not easily soluble diastereoisomer in water, etc. For separating out the not easily soluble diastereomer salt, in addition to cooling the reaction mixture, ordinary methods of solid-liquid separation like filtration can be used.

Any ordinary method can be used for obtaining the optically active form of compound (I) by decomposition of the poorly soluble diastereomer salt form of formula (I). For instance, the diastereomer formula salt (I) can be first mixed with water and dissolved by heating. After this, a mineral acid like HCl can be added and the crystals of the formula (I) that separates out can be filtered.

The present method provides a practical optical resolution of (±) of the formula (II) in high yields of the desired isomer or (+)isomer. In view of the simplicity and cost effective procedure, this improved resolution could be applicable to industrial production of Diltiazem.

The process of the invention is illustrated by the following examples, which are given by way of illustration only and should not be construed to limit the scope of the present invention.

EXAMPLE 1

A 2 liter three necked round bottomed flask fitted with a dropping funnel and a mechanical stirrer is charged with a (±)3-(2-aminophenyl-thio)-2-hydroxy-3-(4'-methoxyphenyl)propionic acid of the formula (II) 100 g (0.313 mole), distilled water (900 ml) and heated on steam bath at 70–80° C. (+)α-Methylbenzylamine of the formula (III) 21.6 ml (0.169 mole) and potassium hydroxide 9.4 g dissolved in 50 ml water were added in small portions alternatively while heating and stirring. After 10–15 min. the mixture becomes a clear solution if necessary immediately filtered hot or decanted and removed unreacted acid. The reaction mixture was stirred further at room temperature for 5 hrs. Then it was cooled in ice bath and the separated solid was filtered and dried to give 57.46 g (83.32%) of (+)α-methylbenzylamine salt of (2S,3S) of the formula (I), m.p. 156–157° C., $[\alpha]_D^{29}$ (+)362.41° (C=0.0241 in 5 ml ethanol).

The above amine salt (2S,3S) of the formula (I) (57.46 g) was treated with benzene 1:6 (343 ml) at 60° C. on steam bath for 15 min, cooled and separated solid was collected and dried to give pure salt of (2S,3S) of the formula (I), 54 g, m.p. 158–159° C., $[\alpha]_D^{29}$ (+)367.33° (C=0.473 g in 100 ml ethanol). (+)α-Methylbenzylamine salt of the formula (2S,3S) (I) (53 g) was taken and suspended in distilled water (2.3 lits) cooled in an ice bath and made acidic with 1 normal HCl (pH 2). The mixture was stirred at room temperature for 1–2 hrs. The separated solid was collected, washed with water and dried to give 32 g (83.2%) of (2S,3S) (I), m.p. 136–138° C., $[\alpha]_D^{29}$ +340.9° (C=0.170 in 5 ml ethanol). The mother liquor obtained after separation of (+)α-methylbenzylamine salt of the formula (I) was treated with 1 normal aqueous HCl while cooling. The crystals formed were filtered out, washed with water and dried to obtain (−)(2R,3R)-3-(2-aminophenylthio)-2-hydroxy-3-(4'-methoxyphenyl)propionic acid m.p. 167–168°, $[\alpha]_D^{23}$ (−)346° (C=0.360 ethanol) optical purity 88%.

EXAMPLE 2

Racemic acid of (2RS,3RS)(2-aminophenylthio)-2-hydroxy-3-(4'-methoxyphenyl)propionic acid of the formula (II), 100 g (0.313 mole) and distilled water (1.5 lits) was placed in the 2 lits flask and heated on steam bath at 70–80° C., (+) α-methylbenzylamine equimolar amount 40.4 g (0.333 mole) was added while heating. After 10–15 min, the mixture becomes a clear solution and stirred further at room temperature for 5 hrs. The salt of the formula (I) formed was filtered and recrystallized from distilled water (900 ml). The separated solid was filtered and dried to give (+) α-methylbenzylamine salt of the formula (I), 56.5 g in (82%) yield, m.p. 157–158° C., $[\alpha]_D^{23}$ (+)376° (C=0.511 in ethanol).

(+)α-Methylbenzylamine salt of (2S,3S) of the formula (I) (49 g) was taken and suspended in distilled water (1900 ml) and the mixture was treated with 2 normal NaOH solution (72 ml) with stirring till a clear solution was obtained. When the solution was turbid it was filtered or decanted. The filtrate was cooled in an ice bath and made acidic with 1 normal HCl (pH 2). The mixture was stirred at room temperature for 1–2 hrs. The separated solid was collected, washed with water and dried to give 31.53 g (88.74%) of (2S,3S) (I), m.p. 136–138° C., $[\alpha]_D^{25}$ (+)343.99° (C=0.25 g in 100 ml ethanol). The purity of the product was verified by HPLC (99.42%).

Recovery of (+)α-methylbenzylamine

The optically active (+)α-methylbenzylamine used for the above separation can be quantitatively recovered and recycled by the following method.

The filtrates obtained from d(+)acid and l(−)acid (Example 1) were combined and made alkaline (pH 10.5) with sodium hydroxide or potassium hydroxide, etc. The amine liberated was extracted with hydrophobic organic solvents like 1,2-dichloroethane, benzene, ether, ethylacetate etc. The combined extracts were dried, the solvent was removed. The crude amine thus obtained was distilled, b.p. 184–186° C., recovery yield 80%, $[\alpha]_D^{27}$ (+)36° (Neat). HPLC purity 99.33%.

EXAMPLE 3

By proceeding in accordance with Example-1, but using Lithium hydroxide 0.80 g (0.019 mole) dissolved in 6.3 ml distilled water, (±) 3-(2-aminophenylthio)-2-hydroxy-3-(4'-methoxyphenylpropionic acid (II), 12.55 g (0.039 moles), distilled water (112 ml) and α-methylbenzylamine (III), 2.75 ml (0.0226 mole), which gave 6.69 g (77.61%), (+) α-methylbenzylamine salt of (2S,3S) of the formula (I), m.p. 156–157° C., $[\alpha]_D^{30}$ (+)318.93° (C=0.494 g in 100 ml ethanol).

The above salt (2S,3S) of the formula (I) 2 g was treated with benzene to give pure salt (2S,3S) of the formula (I), 1.74 g (87%), m.p. 158–159° C., $[\alpha]_D^{30}$ (+)362.31° (C=0.5 g in 100 ml ethanol).

(+)α-Methylbenzylamine salt of (2S,3S) of the formula (I) 1.5 g was suspended in distilled water (33.6 ml) and then treated with 2N NaOH (7.5 ml) and then neutralised with 1 normal HCl (pH 2) to give 0.63 g (58.8%) of (2S,3S)(I), m.p. 137–138° C., $[\alpha]_D^{28}$ (+)341.76° (C=0.23 g in 100 ml ethanol), optical purity 98.77%.

EXAMPLE 4

According to the procedure described in Example-1, but using ammonium hydroxide 3 ml (25%), (±)3-(2-aminophenylthio)-2-hydroxy-3-(4'-methoxyphenyl) propionic acid of the formula (II), 12.56 g (0.039 mole), distilled water (112 ml) and α-methylbenzylamine (III), 2.75 ml (0.022 mole), (+)α-methylbenzylamine salt of (2S,3S) of the formula (I) was obtained 6.43 g (74.59%), $[\alpha]_D^{28}$ (+)323.96° (C=0.486 g in 100 ml ethanol).

The above salt (2S,3S) of the formula (I) 6 g was treated with benzene to give pure salt of (2S,3S)) of the formula (I), 5.5 g (92.58%), m.p. 158–159° C., $[\alpha]_D^{28}$ (+)374.62° (C=0.524 g in 100 ml ethanol).

(+) α-Methylbenzylamine salt of (2S,3S) of the formula (I) 5 g was suspended in distilled water (112 ml) and then treated with 2N NaOH (25 ml) and then neutralized with 1 normal HCl (pH 2) to give 3.24 g (89%) of (2S,3S) (I), m.p. 136–138° C., $[\alpha]_D^{26}$ (+)328.67° (C=0.233 g in 100 ml ethanol). Optical purity 94.99%.

We claim:

1. A process for the optical resolution of racemic (±) (2RS,3RS)-3-(2-aminophenylthio)-2-hydroxy-3-(methoxyphenyl) propionic acid (II) with half mole equivalent of optical resolving agent (+)α-methylbenzylamine (III) and half mole equivalent of an alkali in the presence of a polar solvent at a temperature in the range of 70–80° C.,to form a precipitate of (+)α-methylbenzylamine salt of (2S, 3S) propionic acid (I) with (−) (2R,3R) propionic acid remaining in solution, and then converting the precipitate to the free acid (+) (2S, 3S)-3-(2-aminophenylthio)-2-hydroxy-3-(4-methoxyphenyl) propionic acid (I) giving substantially optically pure form of said propionic acid (I).

2. The process according to claim 1 wherein the alkali is selected from the group consisting of KOH, NaOH, LiOH, NH₄OH, and mixtures thereof.

3. The process according to claim 1 wherein the polar solvent consists of water.

4. The process according to claim 1, wherein the optical resolving agent (+)α-methylbenzylamine (III) and alkali are added simultaneously with stirring to the racemic (±) (2RS, 3RS)-3-(2-aminophenylthio)-2-hydroxy-3-(methoxyphenyl) propionic acid (II) at a temperature in the range of 70–80° C.

5. The process according to claim 1, wherein after addition of optically resolving agent (+)α-methylbenzylamine (III) and the alkali, the reaction mixture is stirred further for a period in the range of 5 to 6 hrs at room temperature.

6. The process according to claim 1, wherein the substantially optically pure propionic acid (I) is purified by recrystallization using a solvent selected from the group consisting of water, methanol, ethanol, acetone, alkanol-water and mixtures thereof.

7. The process according to claim 1, wherein the polar solvent has at least one component selected from the group consisting of water, methanol, ethanol, acetone, benzene, and ethylacetate.

8. The process according to claim 3, wherein the optical resolving agent (+)α-methylbenzylamine (III) and alkali are added simultaneously with stirring to the racemic (±) (2RS, 3RS)-3-(2-aminophenylthio)-2-hydroxy-3-(methoxyphenyl) propionic acid(II) at a temperature in the range of 70–80° C.

9. The process according to claim 3, wherein after addition of optically pure resolving agent (+)α-methylbenzylamine (III) and the alkali, the reaction mixture is stirred further for a period in the range of 5 to 6 hrs at room temperature.

10. The process according to claim 3, wherein the substantially optically pure propionic acid (I) is purified by recrystallization using a solvent selected from the group consisting of water, methanol, ethanol, acetone, alkanol-water and mixtures thereof.

11. The process according to claim 1, wherein the conversion of the precipitate is by using hydrochloric acid (HCl).

12. The process according to claim 11 wherein the conversion includes suspension of the precipitate in distilled water, treatment with sodium hydroxide (NaOH) and neutralization with hydrochloric acid (HCl).

13. The process according to claim 3 wherein the conversion of the precipitate is by using hydrochloric acid (HCl).

14. The process according to claim 13 wherein the conversion includes suspension of the precipitate in distilled water, treatment with sodium hydroxide (NaOH) and neutralization with hydrochloric acid (HCl).

15. The process according to claim 1, wherein the optical resolving agent (+)α-methylbenzylamine (III) and alkali are added in alternating portions while stirring to the racemic (±) (2RS, 3RS)-3-(2-aminophenylthio)-2-hydroxy-3-(methoxyphenyl) propionic acid (II) at a temperature in the range of 70–80° C.

16. A process for the optical resolution of racemic (±) (2RS,3RS)-3-(2-aminophenylthio)-2-hydroxy-3-(methoxyphenyl) propionic acid (II) with half mole equivalent of optical resolving agent (+)α-methylbenzylamine (III) and half mole equivalent of an alkali in the presence of water at a temperature in the range of 70–80° C., to form a precipitate of (+)α-methylbenzylamine salt of (2S,3S) propionic acid (I) with (−) (2R,3R) propionic acid remaining in solution, and then converting the precipitate to the free acid (+) (2S,3S)-3-(2-aminophenylthio)-2-hydroxy-3-(4-methoxyphenyl)propionic acid (I) giving substantially optically pure form of said propionic acid (I) wherein the optical resolving agent (+)α-methylbenzylamine (III) and alkali are added in alternating portions while stirring to the racemic (±) (2RS,3RS)-3-(2-aminophenylthio)-2-hydroxy-3-(methoxyphenyl) propionic acid (II).

* * * * *